United States Patent [19]

Leston

[11] 4,424,381

[45] Jan. 3, 1984

[54] PROCESS FOR SEPARATING DIHYDRIC PHENOLS

[75] Inventor: Gerd Leston, Pittsburgh, Pa.

[73] Assignee: Koppers Company, Inc., Pittsburgh, Pa.

[21] Appl. No.: 372,062

[22] Filed: Apr. 26, 1982

[51] Int. Cl.³ .............................................. C07C 37/68
[52] U.S. Cl. .................................... 568/753; 568/750; 568/766
[58] Field of Search ................. 568/750, 766, 753, 751

[56] References Cited

U.S. PATENT DOCUMENTS

| | | | |
|---|---|---|---|
| 3,981,929 | 9/1976 | Davis et al. | 568/753 |
| 4,267,389 | 5/1981 | Leston | 568/750 |
| 4,267,390 | 5/1981 | Leston | 568/750 |
| 4,267,391 | 5/1981 | Leston | 568/750 |
| 4,267,392 | 5/1981 | Leston | 568/750 |

OTHER PUBLICATIONS

Sharpless et al., "J. Org. Chem.", vol. 40, (1975), pp. 1252–1257.

*Primary Examiner*—Werren B. Lone
*Attorney, Agent, or Firm*—J. Timothy Keane; Daniel J. Long; Herbert J. Zeh, Jr.

[57] ABSTRACT

A process is disclosed for separating closely-boiling dihydric phenol compounds by treating a mixture of dihydric phenols with a metal halide salt. The metal halide salt preferentially forms a complex with one of the dihydric phenols over other related dihydric phenols in the mixture. The preferentially-formed complex of one of the dihydric phenols may then be isolated from the mixture and the complex decomposed to provide a product substantially enriched in, or substantially entirely composed of, one dihydric phenol. The process is particularly suitable for resolving a mixture comprising hydroquinone and catechol, or a mixture of hydroquinone and resorcinol, or a mixture of homocatechol and hydroquinone, or a mixture of catechol and resorcinol.

37 Claims, No Drawings

PROCESS FOR SEPARATING DIHYDRIC PHENOLS

BACKGROUND OF THE INVENTION

1. Field of the Invention

Preferential complexation of one organic compound in a mixture of related compounds is a known technique for resolving mixtures of compounds having close boiling points. Of particular interest herein are methods for resolving mixtures of dihydric phenols by preferential complexation of one of the dihydric phenols.

2. State of the Art

Mixtures of dihydric phenols are available as end-products or by-products of many chemical synthesis reactions, as by-products from purification of tar acid volatile products of coal gasification, and as by-product of pulping operations. For example, in the synthesis of resorcinol or hydroquinone by hydroperoxidation of difficult-to-separate meta-/para-diisopropylbenzenes, a mixture of resorcinol and hydroquinone is obtained in a two-to-one mole ratio. In the oxidation of phenol, a mixture of hydroquinone and catechol is typically produced with the dihydric phenols in a one-to-one mole ratio. In wood operations, catechol and homocatechol are isolated as a mixture from other pulping components. In all of these mixtures of dihydric phenols, the isolation and purification of individual dihydric phenols is very difficult by the use of conventional separation methods such as fractional distillation.

There are chemical processes known for separating closely-boiling organic compounds by methods other than, or in addition to, energy-intensive physical separation techniques such as fractional distillation or fractional crystallization. These chemical processes involve a step of preferential complexation of one component of a mixture of closely-boiling compounds over other components of the mixture. For example, U.S. Pat. No. 4,267,389 to Leston, describes treating a phenolic mixture comprising para-cresol, methylated phenols and ethylated phenols, with an inorganic halide salt, such as calcium bromide, to remove para-cresol from the mixture. Removal of para-cresol from the mixture involves formation of a complex between para-cresol and calcium bromide, which complex forms preferentially over complexes between calcium bromide and other components of the phenolic mixture.

Mixtures of various alcohols may be resolved by treatment with a halide salt. For example, in Sharpless et al., *J. Org. Chem.*, Vol. 40, No. 9, p.p. 1252–1257 (1975), there is reported a study of competition between pairs of mono-hydroxy alcohols and mono-hydroxy phenols for complex formation with a halide salt. This study finds that phenols as a class form poorer complexes than alcohols of comparable melting point, probably because the phenols are weaker bases than the comparable alcohols.

There remains a need, therefore, for methods for resolution of mixtures of closely-boiling dihydric phenols by chemical complexation methods, rather than by fractional crystallization or distillation.

SUMMARY OF THE INVENTION

A mixture of two or more dihydric phenols may be resolved into individual dihydric phenol components by a process involving a step of forming a solid complex preferentially between a metal halide salt and one of the dihydric phenols in the dihydric phenol mixture, in the presence of a liquid aliphatic ether. A metal halide salt suitable for forming the solid complex may be selected from the group consisting of calcium bromide, calcium chloride, lithium bromide, magnesium chloride and magnesium bromide. Resolution of a dihydric phenol mixture may be accomplished by either of the following two preferred methods.

A first method involves bringing together a mixture of two or more dihydric phenols and a selected metal halide salt in the presence of a liquid aliphatic ether solvent, the metal halide being selected such that a complex forms with one of the dihydric phenols in preference to, or preferentially over, other dihydric phenols in the mixture. This preferentially formed complex constitutes a solid material in contact with the liquid aliphatic ether solvent. The solid complex may then be removed or isolated from the liquid ether solvent and thereafter decomposed to a product comprising a predominantly greater amount of the preferentially-complexed dihydric phenol than other dihydric phenols, as compared to the relative amounts of dihydric phenols present in the original mixture. The product may also contain dihydric phenol derived from complexes which form with the selected metal halide salt, but in lesser amount than the amount of dihydric phenol derived from the preferentially-formed complex.

A second method involves forming a mixture of two or more dihydric phenols in a liquid phase in contact with a selected metal halide salt, the metal halide salt initially present in an amount relative to one dihydric phenol and selected such that one or more complexes form between the selected metal halide salt and one or more of the dihydric phenols, but such that at least one of the dihydric phenols forms no complex or forms a significantly lesser amount of complex with the selected metal halide salt than the preferetially-complexed dihydric phenol. This dihydric phenol which forms no complex, or which forms a complex in a significantly lesser amount than other dihydric phenols, relative to amounts of dihydric phenols originally present in the mixture, remains dissolved in the liquid aliphatic ether solvent. The ether solvent may then be removed or isolated from the preferentially-complexed dihydric phenols which are present as solid material. Removal of the ether solvent provides a product containing an enriched amount of the dihydric phenol which did not preferentially complex with the selected metal halide salt, as compared to the original mixture of dihydric phenols.

Mixtures of dihydric phenols susceptible to treatment with the process of the invention include mixtures of two or more dihydric phenols such as catechol, hydroquinone, resorcinol, alkyl-substituted catechols, alkyl-substituted hydroquinones and alkyl-substituted resorcinols.

One advantage provided by the process of the invention is that good resolution or mutual separation of pairs of closely-boiling dihydric phenols can be obtained from a mixture of two or more of such dihydric phenols. The term "closely-boiling" describes dihydric phenols which have boiling points in a relatively narrow range, that is, within a range of 5°–8° C., the separation of which would be substantially impossible to accomplish in a one-stage fractional distillation or separation. A second advantage resides in this chemical-separation process requiring significantly less energy to accomplish good resolution of closely-boiling dihydric phenols than physical-separation methods such as fractional distillation or crystallization.

The chemical-separation process of the invention may also be used advantageously in conjunction with conventional physical-separation processes. For example calcium bromide complexation may be used in an initial treatment of a dihydric phenol mixture for separating the closest-boiling compounds, that is, compounds boiling within a range of about five centigrade degrees. Then, a resulting mixture of compounds having boiling points differing by more than about five centigrade degrees can be treated by distillation or crystallization for more complete resolution of the mixture.

DETAILED DESCRIPTION OF THE INVENTION

The phrases "resolving a mixture of dihydric phenols" and "resolution of a mixture of dihydric phenols" relate to a mechanism or a result in which the individual dihydric phenol components of a mixture containing two or more dihydric phenols may be separated or isolated from each other. Thus, the separation of a significant amount of one dihydric phenol from a mixture of two dihydric phenols constitutes a resolution of the mixture. The phrases also embrace separation of a multi-component mixture into groups of dihydric phenols, each group containing two or more dihydric phenols. Also included within the definition are treatments resulting in a significant increase in the amount of one or more dihydric phenols as compared to the composition of the original mixture of dihydric phenols, even where the original mixture contained relatively small amounts of the dihydric phenol which is found in an enriched amount in the treated mixture. It is contemplated that a differentation or enrichment in the relative amounts of dihydric phenols is a "significant enrichment" if treatment of a mixture provides an increase of at least about 20 weight percent in one or more of the dihydric phenols as compared to the composition of the original mixture.

The phrases "preferentially-formed complex" and "predominantly-complexed dihydric phenol" are intended as abbreviated descriptions of the complex comprising a selected metal halide salt and a dihydric phenol which forms in an amount significantly greater than an amount of any other complex of another dihydric phenol resulting from treatment of the dihydric phenol mixture with the selected metal halide salt. Any complex formed will preferably be comprised substantially entirely of a complex of a single type of dihydric phenol. It is recognized, however, that other dihydric phenols in a starting mixture may form complexes with the selected salt in secondary or lesser amounts than the primary, predominantly-formed complex. Such secondary complex formation in lesser amounts is not deleterious provided that the ratio of the predominant complex to the secondary complex in the resulting solid material is sufficiently high to provide a useful resolution of a dihydric phenol mixture. For example, it is contemplated that a primary-to-secondary or predominant-to-lesser ratio of the relative amounts of dihydric phenol complexes of the treated mixture constitutes a significant and usefully-resolved mixture of dihydric phenols when a ratio of 60-to-40 is obtained as compared to a starting mixture ratio of 50-to-50 of the dihydric phenols.

Mixtures of dihydric phenols suitable for treatment by methods of the invention are available as end-products or by-products of many commercial process operations. Such dihydric phenol mixtures are generated in large quantities as by-products from the purification of tar acid volatile components obtained in many shale oil extraction and coal-gasification operations. A mixture of dihydric phenols which may be resolved by the process of the invention includes practically any mixture of two or more of an unsubstituted dihydric phenol or an alkyl-substituted dihydric phenol having one to four alkyl groups wherein the alkyl groups contain one to about four carbon atoms. The term "dihydric phenol", as used herein, is a short hand term intended to embrace both unsubstituted dihydric phenols and alkyl-substituted dihydric phenols, of the general type described. Examples of unsubstituted dihydric phenols are resorcinol, catechol and hydroquinone. Examples of alkyl-substituted dihydric phenols are 2-methylresorcinol, 4-methylresorcinol, 5-methylresorcinol (orcinol), 2,4-dimethylresorcinol, 3-methylcatechol, 4-methylcatechol (homocatechol), 4-ethylcatechol, 3-isopropylcatechol, 4-t-butylcatechol 3,5-di-t-butylcatechol, 2-methylhydroquinone, 2,3-dimethylhydroquinone, 2,5-dimethylhydroquinone, 2,6-dimethylhydroquinone, 2-ethylhydroquinone, 2,6-diethylhydroquinone, 2,6-diisopropylhydroquinone, 2,5-di-t-butylhydroquinone, and 2,6-di-t-butylhydroquinone.

The family of metal halide salts which may be used in the invention are characterized in having several features in common. For example, in addition to each member of the family being an inorganic salt of a metallic chloride or bromide, these halide salts are characterized in taking on water of hydration. The hydratable nature of these metal halide salts is believed to be significant in the mechanism of complex formation with dihydric phenols, even though no water is involved in the complexation reaction. Of the family of metal halide salts suitable for use in the invention, calcium bromide and calcium chloride are preferred. It is also preferred, whether calcium bromide or calcium chloride or any other of the halide salts is used, that the salt have a water content, either as hydrate or occluded of less than about ten weight percent. Also, it is preferred that the salt have a particle size less than about 200 mesh.

In the complexation reaction involving certain dihydric phenols and calcium bromide or calcium chloride in the presence of an aliphatic ether as a solvent, there is typically formed a ternary complex consisting essentially of the dihydric phenol, the aliphatic ether and the calcium bromide or calcium chloride salt. For example, in complexation reactions involving mixtures of dihydric phenols such as hydroquinone, resorcinol, catechol and homocatechol, ternary complexes can form consisting essentially of the dihydric phenol, the aliphatic ether and halide salt as follows:

catechol:ether:calcium bromide
    homocatechol:ether:calcium bromide
    hydroquinone:ether:calcium bromide
    catechol:ether:calcium chloride
    catechol:ether:magnesium chloride The ether compound which constitutes a component of these ternary complexes may also serve as a solvent for the complexation reaction. Thus, the ether component may be characterized as a "participating solvent" for purposes of describing the invention. Ethers suitable as participating solvents are aliphatic ethers such as diethyl ether, methyl isopropyl ether, methyl t-butyl ether, tetrahydropyran, dioxane and tetrahydrofuran.

In bringing together the components to form a complex, the components can be added together in any order or simultaneously. Typically, the mixture of dihydric phenols may be extracted from an aqueous system by the use of an aromatic hydrocarbon, such as toluene, or by use of an ether as an extracting solvent. It is essential that water be substantially absent from the mixture of dihydric phenols to be treated, in order that the complex may be formed, and thus extractions of dihydric phenols from aqueous system must be done with care. Inasmuch as an ether is an essential component of the complex formed with the preferred halide salts, an ether must be added to the mixture of dihydric phenols in situations where an ether was not used as the extracting solvent for the mixture of dihydric phenols.

The process of the invention is particularly suitable for resolving mixtures containing certain pairs of dihydric phenols. For resolution of such mixtures, the amount of halide salt used is typically expressed in a mole ratio of the preferentially-complexed dihydric phenol-to-halide salt. For example, in a mixture containing hydroquinone and catechol, calcium bromide preferentially complexes with catechol to form an insoluble material. In such mixture, the initial mole ratio of catechol:calcium bromide may be in a range from about 0.2:one to about 5:one. In a mixture of hydroquinone and homocatechol, calcium bromide preferentially complexes with homocatechol to form an insoluble solid. In such mixture, the initial mole ratio of homocatechol:calcium bromide may be in a range from about 0.2:one to about 5:one. In a mixture of resorcinol and hydroquinone, calcium bromide preferentially complexes with hydroquinone. In such mixture, the initial mole ratio of hydroquinone:calcium bromide may be in a range from about 0.2:one to about 5:one. In a mixture of catechol and resorcinol, calcium chloride preferentially complexes with catechol. In such mixture, the initial mole ratio of catechol:calcium chloride may be in a range from about 0.2:one to about 5:one. In a mixture of catechol, resorcinol and hydroquinone, calcium bromide preferentially complexes with catechol. In such mixture, the initial mole ratio of catechol:calcium bromide may be in a range from about 0.2:one to about 5:one. In a mixture of catechol and resorcinol, magnesium chloride preferentially complexes with catechol. In such mixture, the initial mole ratio of catechol:magnesium chloride may be in a range from about 0.2:one to about 5:one.

Generally, the halide salt is added to the mixture of dihydric phenols dissolved in, or in contact with, the ether. For calcium bromide or calcium chloride, for example, the salt is preferably added in amount in a range from about 0.1 mole to about 4 moles to one mole of the dihydric phenol to be preferentially complexed. The ether is added in an amount in excess of that required to form a complex with the desired dihydric phenol and halide salt. Typically if the ether is the solvent for the dihydric phenol mixture, the ether will be present in a ten-fold molar excess of all dihydric phenols. Usually, the complexation reaction takes place in the presence of a catalyst such as a lower aliphatic alcohol. A typical catalytic amount of the alcohol would be approximately five mole percent of the alcohol based on the total dihydric phenol content.

After the aforementioned components are brought together as a mixture, usually in the form of a slurry, the mixture is agitated for a period of time sufficient for the dihydric phenol-ether-halide salt complex to form. A typical mixing time is in a range from about one hour to about 24 hours. Mixing is typically conducted at room temperature and at atmospheric pressure, although the complexation reaction may be conducted at practically any temperature in a range from about 0° C. to about 100° C. At higher temperatures, pressure may be applied to the reaction mixture to maintain the aliphatic ether as a liquid. Also, care must be taken to exclude ambient moisture from the reaction mixture.

After the mixing period, the mixture contains a fluffy, white or gray solid material component in contact with a liquid component. The solid material may be separated from the liquid component by any conventional separation techniques such as by decanting, by centrifugation, or by filtration. If filtration is used to separate the solid material from the liquid, the filtration may be conducted with the aid of pressure gradient applied across the filter medium. The separated solid material may be washed with small portions of an ether, and the washings thereafter may be combined with the filtrate. After the washing step, the separated solid material may be optionally dried, usually by means of low heat or in a desiccator under reduced pressure. The drying step is carried out until the solid material reaches a constant weight.

The solid material, whch contains the dihydric phenol-ether-halide salt complex, is then decomposed to provide the desired dihydric phenol. Decomposition may be accomplished by hydrolysis of the complex in water, by heating of the complex at a temperature usually in a range of from about 150° C. to about 350° C., or by treatment with an alcohol, such as a lower boiling aliphatic alcohol. Preferred decomposition methods include water hydrolysis and heat treatment of the complex. In decomposition of the complex by water hydrolysis, the dihydric phenol may be recovered by treating the water with an organic solvent, typically ether. In decomposition of the complex with heat, the ether component will be separated firstly from the decomposed complex, followed by separation of the dihydric phenol from the halide salt residue. In either of these decomposition methods, the halide salt may be recovered and recycled for treatment of another mixture of dihydric phenols, or for subsequent treatment of the separated dihydric phenols in the event of incomplete separation of the mixture of dihydric phenols.

It is an important feature of the invention that the liquid portion of the mixture treated with the halide salt contains the dihydric phenol which less predominantly forms a complex with the halide salt or which forms substantially no complex with the halide salt. Thus the liquid portion of the treated mixture will be enriched in this dihydric phenol and depleted in the dihydric phenol which predominantly complexes with calcium bromide. This dihydric phenol may be recovered from this liquid portion by conventional distillation or fractionation techniques.

In order to demonstrate the invention a series of individual dihydric phenols were treated with ether and with a halide salt such as calcium bromide to show the formation of the three-component dihydric phenol-ether-halide salt complex, as described in Examples I–V. As shown in Examples VI–XVIII, various synthetic mixtures of two or three dihydric phenols were prepared for treatment with a metal halide salt and ether to show the preferential complexation of one dihydric phenol over another dihydric phenol in the mixture, so as to allow separation of the dihydric phenols. In the working examples which follow, the extracted-and-decomposed complexes of the separated solid material and the liquid portion were subjected to NMR, IR or gas chromatographic analysis to determine the relative amounts of dihydric phenols in the solid material and in the liquid filtrate.

EXAMPLE I

A reaction vessel equipped with stirring means was charged with 11.0 g resorcinol (100 mmole), 0.2 ml absolute ethanol and 77 ml diethyl ether as a solvent for the organic components. To the reaction vessel was added 5.0 g powdered anhydrous calcium bromide (25 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. A complexation reaction was run by stirring this mixture for about 18 hours at room temperature. Then, more ether was added to the mixture which was observed to contain a large amount of fluffy, white solid material suspended in the liquid solution. The mixture was filtered under suction, in a manner to minimize exposure of the mixture to ambient moisture, so as to separate the fluffy solid material from the liquid component. The separated solid material was washed twice with small portions of ether and the ether washings were combined with the filtrate. The washed solid material was dried in a desiccator under a pressure of 1 mm Hg absolute for a period of time until a substantially constant weight was recorded of 6.65 g. A portion of the dried solid material was hydrolyzed in water to form a hydrolyzate. Inasmuch as the filtrate after removal of the ether yielded 9.4 g resorcinol, it was determined that 1.6 g resorcinol complexed with the calcium bromide so that the molar ratio of resorcinol:calcium bromide in the complex was 0.6:1.

EXAMPLE II

A complexation reaction was run generally as described in Example I with a mixture of 11.0 g resorcinol (100 mmole), 0.1 ml absolute ethanol, 110 ml diethyl ether and 5.0 g powdered anhydrous calcium bromide (25 mmole). After the mixture was stirred for 4 hours at room temperature, a washed-and-dried solid material was obtained in an amount of 6.5 g. A portion of the solid material was hydrolyzed in water, the hydrolyzate was extracted sequentially with five portions of diethyl ether and the ether extract was subjected to gas chromatographic analysis, the analysis showed the presence of resorcinol which had complexed with calcium bromide. Ether solvent was removed from the filtrate to give a constant-weight residue of 9.9 g. Inasmuch as 1.1 g resorcinol apparently complexed with 5.0 g $CaBr_2$, it was determined that the 0.4 g difference was attributable to the presence of diethyl ether in the complex.

EXAMPLE III

A complexation reacton was run generally as described in Example I with a mixture of 11.0 g hydroquinone (100 mmole), 0.2 mmole absolute ethanol, 155 ml diethyl ether and 5.0 g powdered anhydrous calcium bromide (25 mmole). After the mixture was stirred for 17 hours at room temperature, a washed-and-dried solid material was obtained in an amount of 8.4 g. The filtrate yielded 9.0 g hydroquinone showing that 2.0 g hydroquinone complexed with calcium bromide for a hydroquinone:calcium bromide mole ratio of 0.7:1.

EXAMPLE IV

A complexation reaction was run generally as described in Example I with a mixture of 11.0 g catechol (100 mmole), 0.2 ml absolute ethanol, 130 ml diethyl ether and 5.0 g powdered anhydrous calcium bromide (25 mmole). After the mixture was stirred for 56 hours, a washed-and-dried solid material was obtained in an amount of 19.6 g. The filtrate yielded 1.06 g catechol showing that 9.94 g catechol complexed with calcium bromide for a catechol calcium bromide molar ratio of 3.6:1. A repeat run of this complexation raction with like amounts of starting materials yielded 20.1 g of solid material. The filtrate yielded 1.09 g catechol showing that 9.91 g catechol complexed for a catechol:calcium bromide mole ratio of 3.6:1.

EXAMPLE V

In order to show the formation of a ternary complex consisting essentially of a dihydric phenol, an aliphatic ether and a metal halide salt, a side-by-side comparative run was made with one mixture containing an aliphatic ether as a solvent for the complexation reaction and the other mixture containing toluene as the complexation reaction solvent, as follows: A first mixture was prepared in a complexation reaction vessel, generally as described in Example I, by mixing together 12.4 g 4-methylcatechol (100 mmole) 0.2 ml absolute ethanol, 5.0 g powdered anhydrous calcium bromide (25 mmole) and 50 ml diethyl ether. After an initial 5-minute stirring period, 50 ml more diethyl ether was added. After a 21-hour mixing period, a final 25 ml portion of diethyl ether was added to the mixture. Solid material, washed and dried as described before, was obtained in an amount of 22.7 g. A second complexation reaction was run with the same starting materials as described for the first mixture, except that in place of diethyl ether as the complexation solvent there was added 100 ml toluene as the solvent. The mixture was heated to and maintained at a temperature of 80°-85° C. for a 21-hour mixing period; heating was required in order to dissolve the 4-methylcatechol in the toluene. Solid material was obtained from the complexation reaction mixture by filtration as described before. The solid material was washed with several small portions of toluene, the washings then combined with the filtrate. Drying of the solid material was accomplished as described before. The filtrate was treated with dilute aqueous sodium hydroxide to extract the 4-methylcatechol, which extract was acidified with dilute aqueous hydrochloric acid and then treated with diethyl ether to extract the 4-methylcatechol. After removal of ether from the filtrate extract, there was obtained 1.9 g 4-methylcatechol, showing that 10.5 g 4-methylcatechol complexed with calcium bromide for a 4-methylcatechol:$CaBr_2$ mole ratio of 3.4:1. Approximately 7.2 g more of solid complex was obtained from the first ether-solvent complexation reaction mixture as compared to the second toluene-solvent complexation reaction mixture. Also, it was observed that for the second reaction mixture, the total weight of the solid complex (15.5 g) and the recovered 4-methylcatechol (1.9 g) was the same as the starting materials (17.4 g). Thus, it was determined that the 7.2 g excess weight of the solid material recovered from the first reaction mixture was attributable to the presence of diethyl ether as a component of a ternary complex formed between 4-methylcatechol and calcium bromide.

EXAMPLE VI

A reaction vessel equipped with stirring means was charged with 5.5 g hydroquinone (50 mmole) and 6.4 g (4-methylcatechol (50 mmole) along with about 0.2 ml absolute ethanol and 110 ml diethyl ether as a solvent for the dihydric phenols to form a solution. To the reaction vessel, there was added 10.0 g finely-ground anhydrous $CaBr_2$ (50 mmole) to form a slurry-like mixture. The reaction vessel was equipped with a drying tube filled with a desiccant, such as anhydrous calcium sulfate, for the purpose of excluding atmospheric moisture from the reaction mixture during the reaction period. The mixture was stirred for about 16 hours at room temperature after which time there was observed a large amount of a fluffy, white solid material suspended in the liquid solution. Then the mixture was filtered under suction, in a manner to minimize exposure of the mixture to ambient moisture, to separate the fluffy solid material from the liquid component. The separated solid was washed twice with 10 ml portions of ether, the washings then combined with the filtrate. The washed solid was dried in a desiccator under a pressure of 1 mm Hg absolute for two hours at room temperature. The dried solid amounted to 21.6 g, a portion of which was hydrolyzed in water to form a hydrolyzate, which hydrolyzate was extracted from the water by five sequential treatments of the water containing the hydrolyzate with ether. Infrared analysis of the ether extract derived from the precipitate showed that the solid material contained predominantly a complex of homocatechol and calcium bromide, Analysis of the filtrate showed predominantly hydroquinone as the dihydric phenol present. Analytical data are summarized in Table I.

EXAMPLE VII

A complexation reaction was run as generally described in Example VI with a starting mixture of 5.5 g hydroquinone (50 mmole), 5.5 g catechol (50 mmole), 0.2 ml absolute ethanol, 80 ml diethyl ether and 10.0 g powdered anhydrous calcium bromide. After the mixture was stirred for about 16 hours at room temperature, a washed-and-dried solid material was obtained in an amount of 22.0 g and a residue from the filtrate was obtained in an amount of 1.90 g. Treatment and analysis of the solid material showed a complex made up substantially entirely of catechol and calcium bromide, while the filtrate contained substantially hydroquinone as the dihydric phenol. Hence, there was substantially complete separation of the two dihydric phenol isomers from each other. Analytical data are summarized in Table I.

EXAMPLE VIII

A complexation reaction was run as generally described in Example VI with a starting mixture of 5.5 g resorcinol (50 mmole), 5.5 g hydroquinone (50 mmole), 0.2 ml absolute ethanol, 75 ml diethyl ether and 10.0 g anhydrous calcium bromide (50 mmole). After the mixture was stirred for 18 hours at room temperature, 14.5 g solid material and 7.0 g filtrate residue were obtained utilizing the described isolation steps. Treatment and analysis of the solid material showed substantially entirely hydroquinone as the dihydric phenol contained in the complex, while resorcinol was predominant in the filtrate residue. Hence, there was substantially complete separation of the two dihydric phenol isomers from each other. Analytical data are summarized in Table I.

EXAMPLE IX

A complexation reaction was run as generally described in Example VI with a starting mixture of 5.5 g resorcinol (50 mmole), 5.5 g catechol (50 mmole), 0.2 ml absolute ethanol, 100 ml diethyl ether and 5.50 g freshly ground anhydrous calcium chloride (50 mmole). After the mixture was stirred for about 16 hours at room temperature, a washed-and-dried solid material was obtained in an amount of 12.57 g and a residue from the filtrate was obtained in an amount of 6.06 g. Treatment and analysis of the solid material showed a complex made up substantially entirely of catechol as the dihydric phenol present, while the filtrate contained substantially resorcinol and a minor amount of catechol as the dihydric phenols present. Hence, there was substantially complete separation of the two dihydric phenol isomers from each other. Analytical data are summarized in Table I.

TABLE I

| | COMPETITIVE COMPLEXING OF DIHYDRIC PHENOLS | | | | |
|---|---|---|---|---|---|
| Example No. | Dihydric Phenols in Initial Mixture | Initial Mixture Components (Mole Ratio) (a)/(b)/salt | Method | Analysis Complex (a)/(b) | Filtrate (a)/(b) |
| VI | (a) hydroquinone | 1/1/1 | NMR | 9/91 | 82/18 |
| | (b) 4-methyl cathecol | | IR | 5/95 | — |
| VII | (a) hydroquinone | 1/1/1 | IR | 0/100 | 100/0 |
| | (b) catechol | | | | |
| VIII | (a) resorcinol | 1/1/1 | NMR | — | 77/23 |
| | (b) hydroquinone | | IR | 0/100 | — |
| IX | (a) resorcinol | 1/1/1 | GC | 0/100 | 97/3 |
| | (b) catechol | | | | |

EXAMPLE X

A complexation reaction was run as generally described in Example VII with a starting mixture of 2.75 g resorcinol (25 mmole), 2.75 g catechol (25 mmole), 0.2 ml absolute ethanol, 30 ml diethyl ether and 5.0 g powdered anhydrous calcium bromide (25 mmole). After an initial one-half hour reaction period with stirring at room temperature, 70 ml more diethyl ether was added. After the mixture was stirred for about 17 hours at room temperature, a washed-and-dried solid material was obtained in an amount of 10.22 g. Treatment and GC analysis of the solid material showed a complex made up substantially of catechol and calcium bromide, while the filtrate contained substantially resorcinol as the dihydric phenol. Hence, there was substantially complete separation of the two dihydric phenol isomers from each other. Analytical data are summarized in Table II.

EXAMPLE XI

A complexation reaction was run as generally described in Example VII with a starting mixture of 2.75 g resorcinol (25 mmole), 2.75 g catechol (25 mmole), 0.2 ml absolute ethanol, 100 ml diethyl ether and 12.5 g powdered anhydrous calcium bromide (125 mmole). After the mixture was stirred for 18 hours at room temperature, 6.89 g solid material was obtained utilizing the described isolation steps. Treatment and GC analysis of the solid material showed substantially catechol as the dihydric phenol contained in the complex, while resorcinol was the only dihydric phenol found in the filtrate residue. Hence, there was substantially complete separation of the two dihydric phenol isomers from each other. Analytical data are summarized in Table II.

EXAMPLE XII

A complexation reaction was run as generally described in Example VII with a starting mixture of 2.75 g resorcinol (25 mmole), 2.75 g catechol (25 mmole), 0.2 ml absolute ethanol, 100 ml diethyl ether and 4.50 g powdered anhydrous calcium bromide (22.5 mmoles). After the mixture was stirred for about 18 hours at room temperature, a washed-and-dried solid material was obtained in an amount of 9.09 g. Treatment ang GC analysis of the solid material showed catechol as the only dihydric phenol complexed with calcium bromide, while the filtrate contained substantially entirely resorcinol as the dihydric phenol. Hence, there was substantially complete separation of the two dihydric phenol isomers from each other. Analytical data are summarized in Table II.

EXAMPLE XIII

A complexation reaction was run as generally described in Example VII with a starting mixture of 2.75 g resorcinol (25 mmole), 2.75 g catechol (25 mmole), 0.2 ml absolute ethanol, 100 ml diethyl ether and 4.75 g powdered anhydrous calcium bromide (23.9 mmole). After the mixture was stirred for about 16 hours at room temperature, a washed-and-dried solid material was obtained. Treatment and GC analysis of the solid material showed a complex made up substantially entirely of catechol and calcium bromide, while the filtrate contained resorcinol only as the dihydric phenol. Hence, there was substantially complete separation of the two dihydric phenol isomers from each other. Analytical data are summarized in Table II.

EXAMPLE XIV

A complexation reaction was run as generally described in Example VII with a starting mixture of 2.75 g (25 mmole) resorcinol, 2.75 g catechol (25 mmole), 0.2 ml absolute ethanol, 100 ml diethyl ether and 7.5 g powdered anhydrous calcium bromide (37.5 mmole). After the mixture was stirred for about 18 hours at room temperature, a washed-and-dried solid material was obtained in an amount of 11.62 g. Treatment and GC analysis of the solid material showed a complex made up substantially entirely of catechol and calcium bromide, while the filtrate contained resorcinol only as the dihydric phenol. Hence, there was substantially complete separation of the two dihydric phenol isiomers from each other. Analytical data are summarized in Table II.

TABLE II

| Example No. | Mole Ratio of Catechol:Resorcinol:$CaBr_2$ in Initial Mixture | Mole Ratio of Catechol:Resorcinol in Solid Material | Mole Ratio of Catechol:Resorcinol in Filtrate |
| --- | --- | --- | --- |
| X | 1:1:1.0 | 97.3:8.7 | 0:100 |
| X | 1:1:0.5 | 93.1:6.9 | 0:100 |
| XII | 1:1:0.9 | 100:0 | 0.3:99.7 |
| XIII | 1:1:0.95 | 98:2 | 0:100 |
| XIV | 1:1:1.5 | 99:1 | 0:100 |

EXAMPLE XV

A reaction vessel equipped as in Example VII was charged with 5.50 g catechol (50 mmole), 5.50 g resorcinol (50 mmole), 5.50 g hydroquinone (50 mmole), 10.00 g powdered $CaBr_2$ (50 mmole), 100 ml diethyl ether and 0.4 ml absolute ethanol. The mixture was stirred for about 16 hours at room temperature with care being taken to exclude atmospheric moisture from the reaction mixture. Solid material was obtained by filtration of the reaction mixture, which material was washed and dried, as described in Example VII, to a constant weight of 22.39 g. Gas chromatographic analysis of the filtrate showed no catechol present, but showed dihydric phenol comprising hydroquinone or resorcinol, or both, present.

EXAMPLE XVI

A reaction vessel equipped as in Example VII was charged with 5.50 g catechol (50 mmole), 5.50 g resorcinol (50 mmole), 5.50 g hydroquinone (50 mmole), 5.00 g powdered anhydrous calcium bromide (25 mmole), 100 ml diethyl ether and 0.4 ml absolute ethanol. The mixture was stirred for about 16 hours at room temperature with care being taken to exclude atmospheric moisture from the reaction mixture. Solid material was obtained by filtration of the reaction mixture, which material was washed and dried, as described in Example VII, to a constant weight of 14.57 g. Gas chromatographic analysis of an ether extract of the hydrolyzate of the solid material showed the presence of 97.5 percent catechol and 2.5 percent hydroquinone and/or resorcinol. Gas chromatographic analysis of the filtrate showed no catechol present, but showed dihydric phenol comprising hydroquinone or resorcinol, or both, present.

EXAMPLE XVII

A reaction vessel equipped as in Example VII was charged with 5.50 g catechol (50 mmole), 5.50 g resorcinol (50 mmole), 4.35 g powdered anhydrous lithium bromide (50 mmole), 100 ml diethyl ether and 0.1 ml absolute ethanol. The mixture was stirred for about 16 hours at room temperature with care being taken to exclude atmospheric moisture from the reaction mixture. Upon filtration of the reaction mixture, much of the solid material formed an oily layer and passed through to the filtrate. A washed and dried solid material was obtained in an amount of 0.7 g. The filtrate was composed of two layers of liquid. Gas chromatographic analysis of the upper and lower layers showed the presence in the upper layer of 27.5 percent catechol and 72.5 percent resorcinol and the presence in the lower layer of 55.9 percent catechol and 44.1 percent resorcinol.

EXAMPLE XVIII

A reaction vessel equipped as in Example VII was charged with 5.50 g catechol (50 mmole), 5.50 g resorcinol (50 mmole), 4.75 g powdered anhydrous magnesium chloride (50 mmole), 100 ml diethyl ether and 0.2 ml absolute ethanol. The mixture was stirred for about 16 hours at room temperature with care being taken to exclude atmospheric moisture from the reaction mixture. Solid material was obtained by filtration of the reaction mixture, which material was washed and dried, as described in Example VII, to a constant weight of 12.00 g. A portion of the solid material was hydrolyzed in water, which hydrolyzate was extracted five times sequentially with portions of ether to extract the dihydric phenol. Gas chromatographic analysis of the extract showed that the solid complex contained 100 percent catechol as the complexed dihydric phenol. Removal of ether from the filtrate provided a residue of 5.53 g which when subjected to gas chromatographic analysis showed that 100 percent resorcinol was present as the dihydric phenol. Hence, there was virtually complete separation of those two dihydric phenols from the original mixture.

Although specific examples of the instant invention have been set forth hereinabove, it is not intended that the invention be limited solely thereto, but is to include all the variations and modifications falling within the scope of the appended claims.

What is claimed is:

1. A process for resolving a mixture of two or more dihydric phenols comprising the step of:
    treating a mixture of two or more dihydric phenols with a metal halide salt selected from the group consisting of calcium bromide, calcium chloride, lithium bromide, magnesium chloride and magnesium bromide, at a temperature of from about 0° C. to about 100° C., in the presence of an aliphatic ether, so as to form preferentially a complex comprised of the selected halide salt, the ether and one of the dihydric phenols;
    whereby the preferentially-formed halide salt-ether-dihydric phenol complex may be isolated and thereafter decomposed to a product comprising a predominantly greater amount of one dihydric phenol over other dihydric phenols present, as compared to the relative amounts of dihydric phenols present in the original mixture of dihydric phenols.

2. The process of claim 1 wherein the dihydric phenols of the mixture may be selected from catechol, hydroquinone resorcinol and alkyl-substituted catechols, hydroquinones, and resorcinols where the alkyl-substituted dihydric phenol contains one to about four alkyl groups and each alkyl group may contain one to about four carbon atoms.

3. The process of claim 1 wherein the aliphatic ether is diethyl ether.

4. The process of claim 1 wherein said selected metal halide salt is calcium bromide.

5. The process of claim 1 wherein said selected metal halide salt is calcium chloride.

6. The process of claim 1 wherein said selected metal halide salt is lithium bromide.

7. The process of claim 1 wherein said selected metal halide salt is magnesium chloride.

8. A process for resolving a mixture of two or more dihydric phenols comprising the step of:
    forming a mixture of two or more dihydric phenols in a liquid phase in contact with a metal halide salt selected from the group consisting of calcium bromide, calcium chloride, lithium bromide, magnesium chloride and magnesium bromide, said mixture having a temperature of from about 0° C. to about 100° C., in relative amounts sufficient to form a complex between the selected metal halide salt and a first dihydric phenol, which complex is insoluble in the liquid phase but such that at least one other of the dihydric phenols either forms no complex with the selected metal halide or forms a complex in a relative amount which is significantly less than the amount of the complex formed with the first dihydric phenol, said other dihydric phenol remaining in the liquid phase.

9. The process of claim 8 wherein said first dihydric phenol is 4-methylcatechol which forms a complex with calcium bromide and wherein said other dihydric phenol is hydroquinone which remains in the liquid phase in a predominantly greater amount than was present in the original liquid phase.

10. The process of claim 8 wherein said first dihydric phenol is catechol which forms a complex with calcium bromide and wherein said other dihydric phenol is hydroquinone which remains in the liquid phase substantially completely as the only dihydric phenol in the liquid phase.

11. The process of claim 8 wherein said first dihydric phenol is hydroquinone which forms a complex with calcium bromide and wherein said other dihydric phenol is resorcinol which remains in the liquid phase in a predominantly greater amount than was present in the original liquid phase.

12. The process of claim 8 wherein said first dihydric phenol is catechol which forms a complex with calcium bromide and wherein said other dihydric phenol is resorcinol which remains in the liquid phase substantially completely as the only dihydric phenol in the liquid phase.

13. The process of claim 8 wherein said first dihydric phenol is catechol which forms a complex with magnesium chloride and wherein said other dihydric phenol is resorcinol which remains in the liquid phase substantially completely as the only dihydric phenol in the liquid phase.

14. A process for resolving a dihydric phenol mixture containing catechol and hydroquinone, the process comprising the steps of:
    (a) bringing together for from about one hour to about 24 hours calcium bromide, an aliphatic ether and a mixture of dihydric phenols comprising catechol and hydroquinone at a temperature of from about 0° C. to about 100° C. in amounts sufficient to form an insoluble solid material in contact with a liquid, the dihydric phenol contained in the solid material being predominantly or substantially entirely catechol present as a calcium bromide-ether-catechol complex, the dihydric phenol contained in the liquid being predominantly or substantially entirely hydroquinone;
    (b) separating the insoluble solid material from the liquid and thereafter treating the material to decompose the complex, whereby a dihydric phenol product is obtained comprising predominantly or substantially entirely catechol.

15. The process of claim 14 further comprising the step of treating the liquid separated from the insoluble solid material to isolate dihydric phenol which comprises predominantly or substantially entirely hydroquinone.

16. The process of claim 14 wherein the molar ratio of catechol:calcium bromide in the starting mixture is in a range from about 0.2:one to about 5:one.

17. The process of claim 14 wherein the aliphatic ether is diethyl ether.

18. A process for resolving a dihydric phenol mixture containing homocatechol and hydroquinone, the process comprising the steps of:
 (a) bringing together for from about one hour to about 24 hours calcium bromide, an aliphatic ether and a mixture of dihydric phenols comprising homocatechol and hydroquinone at a temperature of from about 0° C. to about 100° C. in amounts sufficient to form an insoluble solid material in contact with a liquid, the dihydric phenol contained in the solid material being predominantly or substantially entirely homocatechol present as a calcium bromide-ether-homocatechol complex, the dihydric phenol contained in the liquid being predominantly or substantially entirely hydroquinone;
 (b) separating the insoluble solid material from the liquid and thereafter treating the material to decompose the complex, whereby a dihydric phenol product is obtained comprising predominantly or substantially entirely homocatechol.

19. The process of claim 18 further comprising the step of treating the liquid separated from the insoluble solid material to isolate dihydric phenol which comprises predominantly or substantially entirely hydroquinone.

20. The process of claim 18 wherein the molar ratio of homocatechol:calcium bromide in the starting mixture is in a range from about 0.2:one to about 5:one.

21. The process of claim 18 wherein the aliphatic ether is diethyl ether.

22. A process for resolving a dihydric phenol mixture containing hydroquinone and resorcinol, the process comprising the steps of:
 (a) bringing together for from about one hour to about 24 hours calcium bromide, an aliphatic ether and a mixture of dihydric phenols comprising hydroquinone and resorcinol at a temperature from about 0° C. to about 100° C. in amounts sufficient to form an insoluble solid material in contact with a liquid, the dihydric phenol contained in the solid material being predominantly or substantially entirely hydroquinone present as a calcium bromide-ether-hydroquinone complex, the dihydric phenol contained in the liquid being predominantly or substantially entirely resorcinol;
 (b) separating the insoluble solid material from the liquid and thereafter treating the material to decompose the complex, whereby a dihydric phenol product is obtained comprising predominantly or substantially entirely hydroquinone.

23. The process of claim 22 further comprising the step of treating the liquid separated from insoluble solid material to isolate dihydric phenol which comprises predominantly or substantially entirely resorcinol.

24. The process of claim 22 wherein the molar ratio of hydroquinone:calcium bromide in the starting mixture is in a range from about 0.2:one to about 5:one.

25. The process of claim 22 wherein the aliphatic ether is diethyl ether.

26. A process for resolving a dihydric phenol mixture containing catechol and resorcinol, the process comprising the steps of:
 (a) bringing together for from about one hour to about 24 hours calcium bromide, an aliphatic ether and a mixture of dihydric phenols comprising catechol and resorcinol at a temperature of from about 0° C. to about 100° C., in amounts sufficient to form an insoluble solid material in contact with a liquid, the dihydric phenol contained in the solid material being predominantly or substantially entirely catechol present as a calcium bromide-ether-catechol complex, the dihydric phenol contained in the liquid being predominantly or substantially entirely resorcinol;
 (b) separating the insoluble solid material from the liquid and thereafter treating the material to decompose the complex, whereby a dihydric phenol product is obtained comprising predominantly or substantially entirely catechol.

27. The process of claim 26 further comprising the step of treating the liquid separated from insoluble solid material to isolate dihydric phenol which comprises predominantly or substantially entirely resorcinol.

28. The process of claim 26 wherein the molar ratio of catechol:calcium bromide in the starting mixture is in a range from about 0.2:one to about 5:one.

29. The process of claim 26 wherein the aliphatic ether is diethyl ether.

30. A process for resolving a dihydric phenol mixture containing catechol, hydroquinone and resorcinol, the process comprising the steps of:
 (a) bringing together for from about one hour to about 24 hours calcium bromide, an aliphatic ether and a mixture of dihydric phenols comprising catechol, hydroquinone and resorcinol at a temperature of from about 0° C. to about 100° C., in amounts sufficient to form an insoluble solid material in contact with a liquid, the dihydric phenol contained in the solid material being predominantly catechol present as a calcium bromide-ether-catechol complex, the dihydric phenol contained in the liquid being substantially entirely devoid of catechol;
 (b) separating the insoluble solid material from the liquid and thereafter treating the material to decompose the complex, whereby a dihydric phenol product is obtained comprising predominantly catechol.

31. The process of claim 30 further comprising the step of treating the liquid separated from insoluble material to isolate dihydric phenol which is substantially entirely devoid of catechol.

32. The process of claim 30 wherein the molar ratio of catechol:calcium bromide in the starting mixture is in a range from about 0.2:one to about 5:one.

33. The process of claim 30 wherein the aliphatic ether is diethyl ether.

34. A process for resolving a dihydric phenol mixture containing catechol and resorcinol, the process comprising the steps of:
 (a) bringing together for from about one hour to about 24 hours magnesium chloride, an aliphatic ether and a mixture of dihydric phenols comprising catechol and resorcinol at a temperature of from about 0° C. to about 100° C. in amounts sufficient to form an insoluble solid material in contact with a liquid, the dihydric phenol contained in the solid material being predominantly or substantially entirely catechol present as a magnesium chloride-ether-catechol complex, the dihydric phenol contained in the liquid being predominantly or substantially entirely resorcinol;

(b) separating the insoluble solid material from the liquid and thereafter treating the material to decompose the complex, whereby a dihydric phenol product is obtained comprising predominantly or substantially entirely resorcinol.

35. The process of claim 34 further comprising the step of treating the liquid separated from insoluble solid material to isolate dihydric phenol which comprises predominantly or substantially entirely resorcinol.

36. The process of claim 34 wherein the molar ratio of catechol:calcium bromide in the starting mixture is in a range from about 0.2:one to about 5:one.

37. The process of claim 34 wherein the aliphatic ether is diethyl ether.

* * * * *